United States Patent [19]

Zhou et al.

[11] Patent Number: 6,123,947
[45] Date of Patent: Sep. 26, 2000

[54] HERBAL COMPOSITION AND TREATMENT METHODS

[76] Inventors: James H. Zhou, 38 Blue Cliff, Ter. #299, New Haven, Conn. 06513; Youwei Wang, North Rd 1, Guisan, Hanyang, Wuhan, 430050, China

[21] Appl. No.: 09/350,069

[22] Filed: Jul. 8, 1999

Related U.S. Application Data

[62] Division of application No. 09/049,555, Mar. 27, 1998, Pat. No. 5,997,875.

[51] Int. Cl.⁷ .......................... A61K 35/78; A61K 31/715
[52] U.S. Cl. .......................... 424/195.1; 514/54; 514/863
[58] Field of Search .......................... 424/195.1; 514/863, 514/54

[56] References Cited

U.S. PATENT DOCUMENTS

| | | | |
|---|---|---|---|
| 4,145,416 | 3/1979 | Lachnit-Fixson et al. | 514/170 |
| 5,283,239 | 2/1994 | Koga et al. | 514/23 |
| 5,411,733 | 5/1995 | Hozumi et al. | 424/195.1 |
| 5,560,914 | 10/1996 | Ghoneum et al. | 424/195.1 |
| 5,603,937 | 2/1997 | Kondon et al. | 424/195.1 |
| 5,744,187 | 4/1998 | Gaynor | 426/590 |

FOREIGN PATENT DOCUMENTS

| | | |
|---|---|---|
| 1098310 | 2/1995 | China . |
| 1107059 | 8/1995 | China . |

OTHER PUBLICATIONS

Wu et al. Beijing Shifan Daxue Xuebao, Ziran Kexueban (1982) 2: 57–66 (English abstract only).

Ohmori et al. Chem. Pharm. Bull. (Tokoyo) (1988) 36(11): 4512–18 (abstract only).

*Primary Examiner*—Christopher Tate
*Attorney, Agent, or Firm*—Bachman & LaPointe, P.C.

[57] ABSTRACT

An herbal treatment composition is provided which includes *Sarcandra glabra* and a polysaccharide preferably derived from certain medicinal mushrooms. Methods for treating psoriasis and purpura using the composition are also disclosed.

17 Claims, No Drawings

HERBAL COMPOSITION AND TREATMENT METHODS

This is a Division of application Ser. No. 09/049,555, filed Mar. 27, 1998, now U.S. Pat. No. 5,997,875.

BACKGROUND OF THE INVENTION

The invention relates to an herbal composition and treatment method and, more particularly, to a specific herbal composition which is useful in treating disorders such as psoriasis and purpura.

Psoriasis is a chronic and disturbing skin disorder, which is manifested by various characteristics such as the formation of scaly patches or flat-topped papules that cause itching. The cause of the disorder is unclear, and current treatments include topical fluorinated corticosteroids, vitamin A, and vitamin D, which are prescribed only for suppressive therapy. With approximately 150,000 new cases of psoriasis diagnosed in the United States each year, the need remains for suitable treatments.

Purpura is a condition of the skin marked by purple or livid spots caused by tiny hemorrhages that invade the tissue, occasionally accompanied with gum or nose bleeding, increased bleeding time, prolonged menstruation, anemia, blood in stools, low fever, headache and other infection-like symptoms. Purpura may also occur in the mucous membranes such as the lining of the mouth, and in internal organs. There is no known cure for purpura in current western medicine, and if symptoms persist, corticosteroids such as Prednisone™ are prescribed. Clearly, the need remains for suitable treatments for purpura as well.

In light of the foregoing, it is the primary object of the present invention to provide a composition and method for treating psoriasis.

It is a further object of the present invention to provide a composition and method for treating purpura.

It is a still further object of the present invention to provide a composition and treatment method for treating psoriasis, purpura and other disorders wherein treatment is simple and accompanied by little or no side effects.

Other objects and advantages of the present invention appear hereinbelow.

SUMMARY OF THE INVENTION

In accordance with the present invention, the foregoing objects and advantages have been readily attained.

According to the invention, an herbal treatment composition is provided which comprises *Sarcandra glabra* and a polysaccharide. The polysaccharide is preferably a polysaccharide derived from the group consisting of *Lentinus edodes, Ganoderma lucidum,* and mixtures thereof, preferably including both *Lentinus edodes* and *Ganoderma lucidum* as well as Grifola and Cordyceps.

In further accordance with the present invention, a method for treating psoriasis is provided, which method comprises the steps of providing an herbal treatment composition comprising an ingredient selected from the group consisting of *Sarcandra glabra,* a polysaccharide and mixtures thereof; and administering said composition to a mammal having psoriasis.

In further accordance with the present invention, a method for treating purpura is provided, which method comprises the steps of providing an herbal treatment composition comprising an ingredient selected from the group consisting of *Sarcandra glabra,* a polysaccharide and mixtures thereof; and administering said composition to a mammal having purpura.

DETAILED DESCRIPTION

The invention relates to an herbal treatment composition and several treatment methods. As will be further set forth below, the herbal treatment composition may suitably be provided in the form of a liquid herbal concentrate, a dry powder or powdered herbal concentrate, capsules, tablets, topical sprays cream or ointment and the like, which includes one or more ingredients which have been found to be desirable in accordance with the invention.

In accordance with the present invention, it has been found that *Sarcandra glabra,* particularly when combined with polysaccharides, especially those derived from medicinal mushrooms such as Grifola, *Lentinus edodes* (Shiitaki), Cordyceps and *Ganoderma lucidum* (Reishi) provides excellent results in treatment of psoriasis and purpura.

*Sarcandra glabra* is an herb that grows in Southern China. It has been documented that *Sarcandra glabra* has antiseptic activity and is traditionally used in Chinese medicine for treating inflammation, blood stasis, arthritis, parasite and cold. The chemical composition of *Sarcandra glabra* includes coumarin/furocoumarin and derivatives, flavones, lactones, glucosides and glucans such as sesquiterpenelactone, pelargonidin, and 3-rhamnosylglucoside. *Sarcandra glabra* is non-toxic in humans at therapeutic dosages of about 25 grams. The safe dose as indicated through studies conducted with mice is 51.2 grams per kilogram of body weight.

The polysaccharide and derivatives which combine advantageously with *Sarcandra glabra* include polysaccharides, oligosaccharides, lectin, glucans, glycans, peptide/protein associated poly or oligosaccharides or glycans/glucans, and derivatives thereof which are collectively referred to herein as polysaccharides. Specific polysaccharides preferably include glucose, arabinose, mannose, xylose, galactone, and the like, and mixtures thereof.

It is further preferred that the composition include some crude extract of one or more of the aforementioned medicinal mushrooms, most preferably of Ganoderma and Cordyceps, so as to include in the composition additional diverse biologically active compounds including additional polyssacharides, glucans, glycans, balanoides, balanol, ophiocordin, ophioglossoides, lectins, lanostane/derivatives, triterpenoids/derivatives, various vitamins, amino acids and minerals.

According to the invention, the herbal treatment composition preferably includes the aforesaid polysaccharide or polysaccharide derivatives in effective amounts, and likewise an effective amount of *Sarcandra glabra.* Although the composition can be provided having a concentration or content of *Sarcandra glabra* which is tailored specific to the particular patient and condition being treated, the herbal treatment composition of the present invention preferably includes *Sarcandra glabra* in a concentration of at least about 10 mg/ml or g, and is administered in treatment amounts of about 1–1.5 ml or g depending upon the form of the composition. Composition amounts may therefore be referred to herein as weights per unit composition.

The herbal treatment composition in accordance with the present invention, as set forth above, includes polysaccharide or polysaccharide derivative, which may preferably be provided from Grifola and/or *Lentinus edodes,* most preferably from a mixture of both. These polysaccharides and derivatives are a group of chain molecules which can be extracted from various sources, most preferably from edible mushrooms such as Cordyceps, *Ganoderma lucidum* (Reishi), *Lentinus edodes* (Shiitaki), Grifola, hericium, poria, and the like, and mixtures thereof, most preferably from a combination of Cordyceps, *Ganoderma lucidum, Lentinus edodes* and Grifola. This group of chain molecules includes polysaccharides, oligosaccharides, lactins, glucans, glycans, peptide/protein associated poly or oligosaccharides or glycans/glucans, and mixtures thereof. The polysaccharide consists chemically of glucose, arabinose, manose, xylose and galactone.

The composition of the present invention preferably includes polysaccharide or derivatives thereof derived or extracted from Grifola and *Lentinus edodes* mushrooms, and most preferably includes a portion of Grifola, Cordyceps, *Lentinus edodes* and *Ganoderma lucidum* mushrooms, each of which may contribute to the total polysaccharide content of the composition, and further which mushrooms may themselves be present in the final composition in the form of crude extract of mushrooms. Crude extract portions of the mushrooms include those portions which are soluble in water/ethanol.

In further accordance with the present invention, the herbal treatment composition most preferably includes a concentration of *Sarcandra glabra* of between about 10 and about 600 mg/ml or mg/g, a concentration of *Lentinus edodes* of between about 5 and about 200 mg/ml or g, and a concentration of *Ganoderma lucidum* of between about 3 and about 450 mg/ml or g. The composition preferably includes polysaccharide or derivatives and mushrooms as set forth above, for example as crude extract, in amounts sufficient to provide polysaccharide in the composition of the present invention in concentrations of between about 5 and about 1000 mg/ml or g.

The herbal treatment composition of the present invention has been found to have excellent results in treating psoriasis and purpura, and may further be useful for treating other disorders, diseases and the like. In treating psoriasis and/or purpura, the herbal treatment composition of the present invention may suitably be administered to a mammalian patient either orally as a liquid or powder concentrate to be added to a liquid, or in pill, capsule or tablet form, or topically as a spray, cream, ointment or the like. For example, the treatment composition of the present invention may be provided in a standardized formula containing *Sarcandra glabra* at a concentration of between about 10 and about 600 mg/g or ml and polysaccharides in a concentration of between about 5 and about 1000 mg/g or ml, and this standardized formula can be administered to a patient for example in 1–1.5 gram dosages of formula, several times per day. In accordance with the present invention, it has been found that such a regimen or treatment method advantageously provides for improvement in psoriasis and purpura conditions, and further does not appear to have any side effect or undesirable result.

The composition of the present invention preferably contains the desired ingredients as follows:

| | |
|---|---|
| *Sarcandra glabra* | 10–30% wt |
| *Ganoderma lucidum* | 15–30% wt |
| Cordyceps | 5–15% wt |
| *Lentinus edodes* | 5–25% wt |
| Grifola | 5–25% wt |

In addition, the composition of the present invention preferably includes between about 5% wt and about 45% wt of the desired polysaccharide or polysaccharide derivatives, which are present from one or more of the mushroom components of the composition of the present invention. These values are provided on the basis of the entire composition, prior to mixing with liquid or powder carriers or solvents and the like.

It should be noted that the term polysaccharide as used herein is specifically intended to include polysaccharide derivatives such as those described above.

The following clinical data shows the excellent results obtained using the herbal treatment composition in accordance with the present invention to treat humans suffering from psoriasis and purpura.

EXAMPLE 1

This example sets forth a clinical study in connection with the skin disorder classified as psoriasis. A test population of 58 people who were classified as having psoriasis were included in a study. This group included 43 males and 15 females. The patients ranged in age from 5–79 years old, and 76% of the patients were in the range of 16–35 years in age. Of the patients tested, 45 had psoriasis for about 2 years prior to the study. Others in the group had the disorder for periods of 1 year to 25 years. This group of patients was classified as patients having common type psoriasis, and 40 of the test cases were in a first clinic admission, while others had experienced remittent psoriasis 2–10 times during the course of their life time.

The protocol of treatment consisted of administering 1–1.5 grams of dry powder having a composition as follows:

| | |
|---|---|
| *Sarcandra glabra* | 28% |
| Mushrooms and polysaccharide | 72% |
| Ganoderma | 27% |
| Cordyceps | 15% |
| Lentinus and Grifola (as crude extract) | 18% |
| Polysaccharide | 12% |

The composition was given orally 3 times per day for 3 months. No other topical or internal treatment was applied during the period of this testing. At the end of the 3 month period, itching and size of scaly patches and flat-topped papules were measured. The results can be classified into three groups. In group 1, 38 of the patients showed 99% to 100% restoration of normal skin health, and had no itching complaint, no visible scaly patches or flat-topped papules, or only tiny spots of same when subjected to close observation. In group 2, 14 of the cases showed an improved condition indicated by more than 50% restoration of normal skin health, no complaint of itching, and reduction of scaly patches and papules by more than 50% of original size. A third group containing the remaining 6 patients showed a lesser response, showing less than 50% restoration of normal skin health and reduced but continuous itching and less than 50% reduction in the size of scaly patches or papules.

No obvious side effects were observed in any of the 58 patients. No discomfort complaints were registered by any patient, and no symptom rebounding was observed during or after the treatment. Further, all liver, blood and urine examinations showed normal signs after the treatment.

From this clinical study, it can be concluded that the treatment composition of the present invention provided a complete response for 65.5% of the patient population, and at least significant improvement in a total of 89.6% (Groups 1 and 2 of the patient population).

Of the 38 cases in group 1, short term post treatment follow ups were conducted and showed no symptomatic rebound. This suggests that the restoration is not due to remittent effect, but instead is due to the treatment of the present invention.

EXAMPLE 2

This clinical study demonstrates use of the treatment composition and method of the present invention to treat purpura. Twenty six people who were classified as having purpura were included in this study. These 26 patients broke down as 10 acute cases, and 16 chronic cases. The 26 people population consisted of thirteen males and thirteen females, and age of the patients ranged from 3 years to 31 years. The majority of patients tested had had the disease for about 2 years. Several others had had the disease from a period of about 2 days to about 10 years. These 26 people were classified as patients having common type purpura, some accompanied with dizziness and fatigue. The platelet counts of these patients ranged from 36,000 to 80,000/mm$^3$.

A dry powder of the composition of the present invention having a composition as set forth in Example 1 was administered to each patient in the study group. The standardized formula was administered three times per day, orally, in treatment amounts of 1–1.5 grams, for a period of 45 days. The acute cases of the test group were treated 4 times per day. Bleeding time and purple or livid spots on the skin were measured both during and after the treatment. Platelet count was examined on the tenth day of treatment.

Purple or livid spots on the skin disappeared in all patients of the group in 7 to 15 days from the beginning of the treatments. Platelet counts of all patients had increased by 10,000/mm$^3$ after 10 days of treatment. Bleeding time had become normal at the end of the treatment. Further, no obvious side effects were observed and no noticeable discomfort complaints were registered. All liver, blood and urine examinations showed normal after the treatment, and no symptom rebounding was observed after the treatment.

This clinical study indicates that the treatment composition of the present invention is in fact effective in responding to the skin disorder classified as purpura. Favorable response in the 26 testers was 100%, and short term (6 months) post treatment follow up of all testers indicated no symptomatic rebound.

In light of the foregoing Examples 1 and 2, it is concluded that the treatment composition in accordance with the present invention is effective for advantageously treating conditions such as psoriasis and purpura. Furthermore, other advantageous applications for this composition may be developed.

A further description of the *Sarcandra glabra* ingredient of the composition of the present invention can be found in the following: The Encyclopedia of Traditional Chinese Medicine (Jiagsu New Medical College, Zhongyao Dachidian), Peoples Publishing Company, Shanghai pages 42–3 (1986); Li et al. "Diagnostic significance of the Cuticular Patterns on Leaf Surface of *Sarcandra Glabra*, Yao Hsueh Hsueh Pao 1990, 25(9): 717–20; Wang et al. "A New Sesquiterpene Lactone from *Sarcandra Glabra*", Yao Hsueh Hsueh Pao January 1988; 23(1): 64–6.

A further description of Grifola mushrooms can be found in several references including: Chang R. "Functional Properties of Edible Mushrooms" [Review] [22 refs.] Nutr. Rev Nov; 54 (11 Pt 2): S91–3, 1996; Miura N N, etc. "Blood Clearance of (1–3)-beta-D-glucan in MR1 1 pr/1pr mice." FEMS Immunol Ded Microbiol, 13(1):51–57, January 1996; Yadoma T. "Enhancement of Cytokine Production by Macrophages Stimulated with (1–3)-beta-D-glucan, Grifolan (GRN), isolated from *Grifola frodosa.*" Biol Pharm Bull; 17 (12):1554–60, 1994.

Further description of Cordyceps mushrooms to be used as an ingredient in accordance with the present invention can be found in the following references: Kuo, Y C and Tsai, W. J. "*Cordyceps Sinensis* as an Immunomodulatory GEN" AM J Chin Med, 24(2): 111–25, 1996; Manabe, N. and Sugimoto, M. "Effects of the Mycelial Extract of Cultured *Cordyceps Sinensis* on in Vivo Hepatic Energy Metabolism in a Mouse.: Jpn J Pharmacol 70(1): 85–8, 1996; Yin, D. and Tang, X "Advances in the Study on artificial cultivation of *Cordyceps Sinensis.*" Chung Kuo Chung Yao Tsa Chih 20(12); 707–9, December 1995.

Further description of the Ganoderma ingredient of the composition of the present invention can be found in the following references: Van de hem L G, et al. "Ling Zhi-8: Studies of a New Immunomodulating Agent." Transplantation, 15;60(5): 438–43, September 1995; Yamawai, M N. and Shimada, A. "A Lectin from Mycelia of the Fungus *Ganoderma Lucidum*" Phytochemistry 44(1) :7–10, January 1997; Cuella, N. J. J. and Giner, R. M. "Two Fungal Lanostane Derivative as Phospholipase A2 Inhibitor." J Nat Prod; 59(10):977–9, October 1996.

Further references can be found in connection with the Lentinus ingredient of the composition of the present invention in the following publications: Tamura, R. and Tanebe, K. "Effects on Lentinan on Abnormal Ingestive Behaviors Induced by Tumor Necrosis Factor." Physio Behav 61(3) :399–410, March 1997; Chang, R. "Functional Properties of Edible Mushrooms" Nutr Rev 54(11 Pt @):S91–3 November 1996; Jin M. and Kim, S. "Induction of B cell Proliferation and NF-kappa B Activation by a Water Soluble Glycan from Lentinus Lepideus." Int J. Immunopharmacol; 18 (8–9): 439–48, 1996 Arg-Sep.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A therapeutic herbal composition comprising *Sarcandra glabra* extract and polysaccharide-containing extracts from the mushrooms Grifola and *Lentinus edodes,* wherein the *Sarcandra glabra* extract and the polysaccharide-containing extracts are in amounts effective to treat psoriasis and purpura.

2. The composition according to claim 1, wherein the composition further comprises extracts of *Ganoderma lucidum* and Cordyceps.

3. The composition according to claim 1, wherein said *Sarcandra glabra* extract comprises coumarin or furocoumarin, flavones, lactones, glucosides and glucans.

4. The composition according to claim 1, wherein said *Sarcandra glabra* extract is present in a concentration of at least about 10 mg per unit composition.

5. The composition according to claim 1, wherein said *Sarcandra glabra* extract is present in a concentration of between about 10 and about 600 mg per unit composition.

6. The composition according to claim 1, wherein the polysaccharides in said polysaccharide-containing extracts are present in a concentration of at least about 5 mg per unit composition.

7. The composition according to claim 1, wherein the polysaccharides in said polysaccharide-containing extracts are present in a concentration of between about 5 and about 1000 mg per unit composition.

8. The composition according to claim 1, wherein said composition is a liquid.

9. The composition according to claim 1, wherein said composition is a dry powder.

10. A therapeutic herbal composition for treating psoriasis and purpura comprising *Sarcandra glabra* extract and polysaccharide-containing mushroom extracts, based on the total weight of said extracts, as follows:

| | |
|---|---|
| *Sarcandra glabra* extract | 10 to 30% wt |
| *Ganoderma lucidum* extract | 15 to 30% wt |
| Cordyceps extract | 5 to 15% wt |
| *Lentinus edodes* extract | 5 to 25% wt |
| Grifola extract | 5 to 25% wt | wherein said composition contains between about 5% wt and about 45% wt polysaccharides from said polysaccharide-containing mushroom extracts.

11. The composition according to claim 10, wherein said *Sarcandra glabra* extract comprises coumarin or furocoumarin, flavones, lactones, glucosides and glucans.

12. The composition according to claim 10, wherein said *Sarcandra glabra* extract is present in a concentration of at least about 10 mg per unit composition.

13. The composition according to claim 10, wherein said *Sarcandra glabra* is present in a concentration of between about 10 mg and about 600 mg per unit composition.

14. The composition according to claim 10, wherein the polysaccharides in said polysaccharide-containing mushroom extracts are present in a concentration of at least about 5 mg per unit composition.

15. The composition according to claim 10, wherein the polysaccharides in said polysaccharide-containing mushroom extracts are present in a concentration of between about 5 mg and about 1000 mg per unit composition.

16. The composition according to claim 10, wherein said composition is a liquid.

17. The composition according to claim 10, wherein said composition is a dry powder.

* * * * *